(12) United States Patent
Cunliffe et al.

(10) Patent No.: US 10,758,171 B2
(45) Date of Patent: Sep. 1, 2020

(54) TOOLS FOR TRACKING THE GUM LINE AND DISPLAYING PERIODONTAL MEASUREMENTS USING INTRA-ORAL 3D SCANS

(71) Applicant: 3M INNOVATIVE PROPERTIES COMPANY, St. Paul, MN (US)

(72) Inventors: Alexandra R. Cunliffe, St. Paul, MN (US); Guruprasad Somasundaram, St. Paul, MN (US); Benjamin D. Zimmer, Maplewood, MN (US); Steve Lastavich, St. Paul, MN (US); Peter See, Berlin (DE); Kelly L. Stein, New Brighton, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/405,215

(22) Filed: May 7, 2019

(65) Prior Publication Data

US 2019/0254588 A1 Aug. 22, 2019

Related U.S. Application Data

(63) Continuation of application No. 15/643,646, filed on Jul. 7, 2017, now Pat. No. 10,327,693.

(51) Int. Cl.
*A61B 5/00* (2006.01)
*A61C 19/04* (2006.01)
(Continued)

(52) U.S. Cl.
CPC .......... *A61B 5/4552* (2013.01); *A61B 5/0088* (2013.01); *A61B 5/1077* (2013.01);
(Continued)

(58) Field of Classification Search
CPC ... A61B 5/4552; A61B 5/7425; A61B 5/1079; A61B 5/1077; A61B 5/0088;
(Continued)

(56) References Cited

U.S. PATENT DOCUMENTS 6,201,880 B1 3/2001 Elbaum et al.
7,077,647 B2 7/2006 Choi et al.
(Continued)

FOREIGN PATENT DOCUMENTS

EP 30505341 1/2016

OTHER PUBLICATIONS

Written Opinion of the Int'l Searching Authority, PCT/IB2018/054713, dated Oct. 19, 2018.
(Continued)

*Primary Examiner* — Brenda C Bernardi

(57) ABSTRACT

Methods for tracking gum line changes by comparing digital 3D models of teeth and gingiva taken at different times. The digital 3D models are segmented to digitally identify the teeth from the gingiva, and the segmented digital 3D models are compared to detect gum line changes by determining differences between them relating to the gum line. Gum line changes can also be estimated by comparing one of the digital 3D models with a 3D model having a predicted original location of the gum line. Gum line change maps can be displayed to show the gum line changes determined through the tracking or estimating of changes. The digital 3D models can also be displayed with periodontal measurements placed upon them.

17 Claims, 4 Drawing Sheets

(51) Int. Cl.
  *A61B 5/107* (2006.01)
  *A61C 9/00* (2006.01)
  *G16H 30/00* (2018.01)
  *G16H 50/50* (2018.01)
  *G16H 50/20* (2018.01)
  *G16H 30/40* (2018.01)

(52) U.S. Cl.
  CPC .......... *A61B 5/1078* (2013.01); *A61B 5/1079* (2013.01); *A61B 5/4842* (2013.01); *A61B 5/7275* (2013.01); *A61B 5/743* (2013.01); *A61B 5/7425* (2013.01); *A61C 9/0046* (2013.01); *A61C 9/0053* (2013.01); *A61C 19/04* (2013.01); *A61C 19/043* (2013.01); *G16H 30/00* (2018.01); *G16H 30/40* (2018.01); *G16H 50/20* (2018.01); *G16H 50/50* (2018.01)

(58) Field of Classification Search
  CPC ..... A61B 5/743; A61B 5/7275; A61B 5/1078; G16H 30/00; A61C 19/04; A61C 9/0046; A61C 9/0053; A61C 19/043
  See application file for complete search history.

(56) References Cited

U.S. PATENT DOCUMENTS

| | | |
|---|---|---|
| 7,442,041 B2 | 10/2008 | Imgrund et al. |
| 7,471,821 B2 | 12/2008 | Rubbert et al. |
| 7,695,278 B2 | 4/2010 | Sporbert et al. |
| 7,826,646 B2 | 11/2010 | Pavlovskaia et al. |
| 8,075,306 B2 | 12/2011 | Kitching et al. |
| 8,244,028 B2 | 8/2012 | Kuo et al. |
| 8,275,180 B2 | 9/2012 | Kuo |
| 9,737,257 B2 | 8/2017 | Ribnick et al. |
| 2009/0316966 A1 | 12/2009 | Marshall et al. |
| 2014/0348405 A1 | 11/2014 | Chen et al. |
| 2015/0319326 A1 | 11/2015 | Pfeiffer et al. |
| 2016/0070821 A1 | 3/2016 | Somasundaram et al. |
| 2016/0135925 A1 | 5/2016 | Mason et al. |
| 2016/0220173 A1 | 8/2016 | Ribnick et al. |
| 2016/0220200 A1 | 8/2016 | Sandholm et al. |
| 2017/0169562 A1 | 6/2017 | Somasundaram et al. |
| 2017/0340414 A1 | 11/2017 | Janzadeh et al. |
| 2018/0235437 A1 | 8/2018 | Ozerov et al. |

OTHER PUBLICATIONS

International Search Report, PCT/IB2018/054713, dated Jun. 26, 2018.

US 10,758,171 B2

1

TOOLS FOR TRACKING THE GUM LINE AND DISPLAYING PERIODONTAL MEASUREMENTS USING INTRA-ORAL 3D SCANS

BACKGROUND

Periodontal health is an important contributor to overall patient health and is tracked both qualitatively and quantitatively during routine dental examinations. Improvements in periodontal tracking are enabled by intra-oral scanners and specifically by the 3D computerized models of dentitions that this technology produces. Digital 3D impressions provide both a display of teeth and gums and quantitative measurements that can be compared with either previous measurements or with standards to indicate issues with periodontal health that may require intervention.

SUMMARY

A method for tracking gum line changes, consistent with the present invention, includes receiving first and second digital 3D models of teeth and gingiva taken at different times. The first and second digital 3D models are segmented to digitally identify the teeth from the gingiva and generate gingiva segmented first and second digital 3D models, and the segmented first and second digital 3D models are compared to detect gum line changes by determining differences between the digital 3D models where the differences relate to the gum line. The method also includes displaying an indication of the gum line changes.

A method for displaying periodontal measurements, consistent with the present invention, includes receiving first and second digital 3D models of teeth and gingiva taken at different times. The first and second digital 3D models are segmented to digitally identify the teeth from the gingiva and generate gingiva segmented first and second digital 3D models. The method also includes receiving periodontal measurements relating to the first or second digital 3D model and displaying the periodontal measurements placed upon the first or second digital 3D model.

A method for estimating gum line changes, consistent with the present invention, includes receiving a digital 3D model of teeth and gingiva, and segmenting the digital 3D model to digitally identify the teeth from the gingiva and generate a gingiva segmented digital 3D model. The method also includes predicting an original location of the gum line in the digital 3D model to obtain a digital 3D model of a predicted original location, and comparing the gingiva segmented digital 3D model with the digital 3D model of the predicted original location to estimate gum line changes.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

The use of digital 3D models in the dental market is becoming more prevalent. These models can be acquired in vivo using an intra-oral scanner or off-line by laser scanning of a traditional impression. The digital 3D models can be used for varied clinical tasks including treatment planning in diagnostic aides, for example to track gum line changes.

Figure 1:
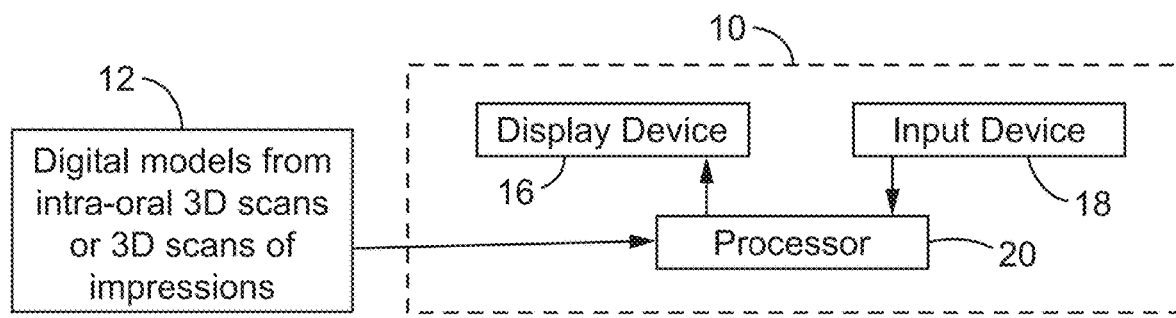
FIG. 1 is a diagram of a system for detecting gum line changes using a digital 3D model based upon intra-oral 3D scans or 3D scans from impressions.
Figure 2:
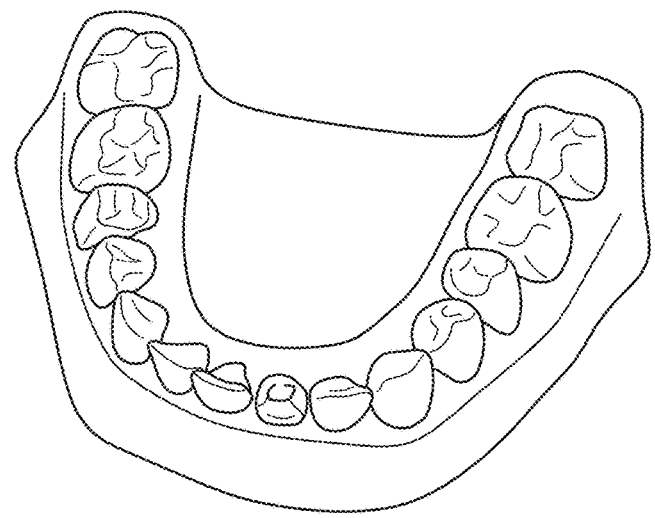
FIG. 2 illustrates a 3D model of teeth and gingiva from intra-oral scans.

FIG. 1 is a diagram of a system 10 for tracking the gum line and estimating gum line changes using a digital 3D model based upon intra-oral 3D scans. System 10 includes a processor 20 receiving digital 3D models of teeth (12) from intra-oral 3D scans or scans of impressions of teeth. System 10 can also include an electronic display device 16, such as a liquid crystal display (LCD) device, and an input device 18 for receiving user commands or other information. An example of digital 3D model of a patient's teeth and gingiva from a scan is shown in FIG. 2. Systems to generate digital 3D images or models based upon image sets from multiple views are disclosed in U.S. Pat. Nos. 7,956,862 and 7,605,817, both of which are incorporated herein by reference as if fully set forth. These systems can use an intra-oral scanner to obtain digital images from multiple views of teeth or other intra-oral structures, and those digital images are processed to generate a digital 3D model representing the scanned teeth and gingiva. System 10 can be implemented with, for example, a desktop, notebook, or tablet computer. System 10 can receive the 3D scans locally or remotely via a network.

The 3D scans addressed herein are represented as triangular meshes. The triangular mesh is common representation of 3D surfaces and has two components. The first component, referred to as the vertices of the mesh, are simply the coordinates of the 3D points that have been reconstructed on the surface—i.e., a point cloud. The second component, the mesh faces, encodes the connections between points on the object and is an efficient way of interpolating between the discrete sample points on the continuous surface. Each face is a triangle defined by three vertices, resulting in a surface that can be represented as a set of small triangular planar patches.

Figure 3:
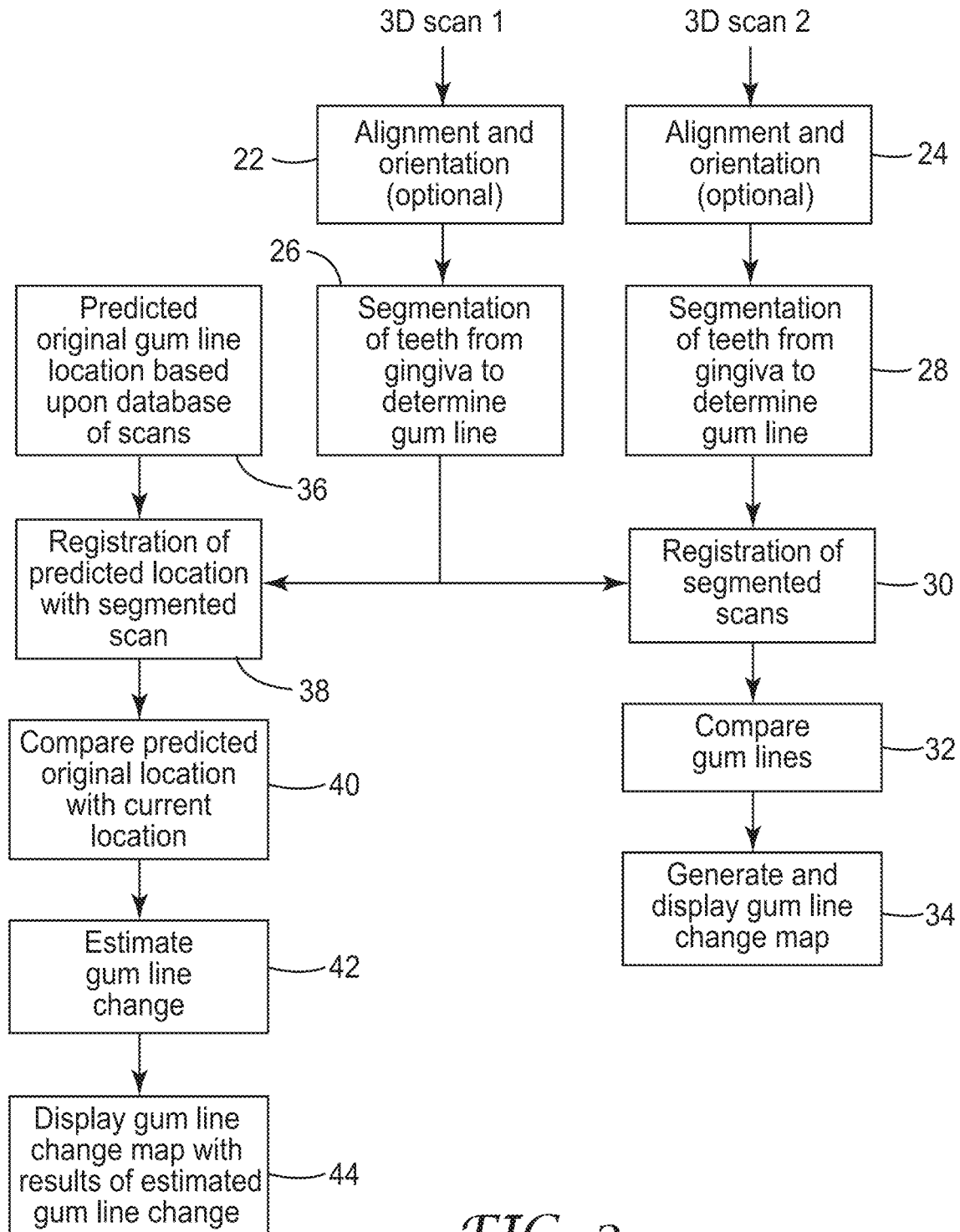
FIG. 3 is a flow diagram of a method to track the gum line and estimate gum line changes using 3D scans.

FIG. 3 is a flow diagram of a method to track the gum line and estimate gum line changes using 3D scans. The method in the flow diagram of FIG. 3 can be implemented in software or firmware modules, for example, for execution by processor 20, and can alternatively be implemented in hardware modules or a combination of software and hardware. This method includes receiving a first 3D scan of a patient's teeth and gingiva, 3D scan 1, optionally aligning and orienting 3D scan 1 (step 22), and segmenting the teeth from the gingiva in 3D scan 1 to determine the gum line (step 26). This method also includes receiving a second 3D scan of the same patient's teeth and gingiva, 3D scan 2, optionally aligning and orienting 3D scan 2 (step 24), and segmenting the teeth from the gingiva in 3D scan 2 to determine the gum line (step 28). In this method, 3D scan 2 is taken at a different time than 3D scan 1, typically a later time. Only two 3D scans from different times are recited for illustrative purposes. The method can be used to process many 3D scans taken at different times over a particular time period. For example, each time a patient visits a dental office, the patient's teeth and gingiva can be scanned, and those 3D scans over time can be processed through this method. The method can also be used to compare 3D scans between different patients or between a single patient and one or more typical patient models of teeth and gingiva.

The method processes the 3D scans by registering the gingiva segmented 3D scan 1 with the gingiva segmented 3D scan 2 (step 30). That registration of the gingiva segmented 3D scans is used to compare the gum lines (step 32) and generate a gum line change map (step 34). Instead of using a registration algorithm, the 3D scans can be compared in other ways.

Instead of or in addition to comparing scans of a person's teeth and gingiva, this method can also predict gum line changes. An original gum line location is predicted based upon a database of scans (step 36). In order to accomplish this, a large database of 3D tooth and gingiva models can be accessed and used, where the gum line location in each of the scans in the database is known. A model from the database can be selected based upon characteristics of a corresponding patient. Given this database, an aggregate generic mathematical model can be formed of the canonical original gum line location. Given this database and the mathematical models learned from it, the original gum line location from the current scan can be predicted. Several approaches exist for performing this step. One approach is as follows. First, the appropriate model from the database for the current scan is determined. Then, a mapping is computed from the model teeth and gingiva to the current teeth and gingiva. This mapping can be accomplished through use of a registration algorithm (step 38). Using this mapping, the model gum line is mapped to the space of the current teeth and gingiva, resulting in a prediction of the original location of the gum line.

Once the original gum line location has been estimated, it can be compared with the actual gum line location in order to assess the amount of gum line change. Then, the areas in which the actual and predicted models are in disagreement must be located and compared (step 40). The comparison results in an estimate of gum line change based upon, for example, a degree or amount of separation from the original predicted gum line location and the current gum line location (step 42). A gum line change map with the results of the estimated gum line change can be displayed (step 44).

The optional alignment and orientation for steps 22 and 24 involve rotating and translating the 3D scans to align them with a particular coordinate system. For example, in a 3D coordinate system, the 3D scans can be aligned substantially parallel with the XZ plane with the teeth pointing up along the Y-axis. The 3D scans can be aligned in other ways. Aligning and orienting the 3D scans can facilitate further processing of multiple scans, for example segmentation and registration of the 3D scans. Examples of methods to align and orient 3D scans are disclosed in U.S. Patent Application Publication No. 2016/0070821, which is incorporated herein by reference as if fully set forth. In some cases, a software interface can be presented in order for a user to perform alignment, or a portion of it, manually.

Segmenting the teeth from the gingiva for steps 26 and 28 involves detecting the gum line in the 3D scans to digitally identify the boundary between the teeth and gingiva to generate a gingiva segmented digital 3D model. This digital identification for segmentation can include, for example, digitally separating the teeth from the gingiva, or using a curve or other indicia on the digital 3D model to distinguish between the teeth from the gum.

Table 1 provides exemplary pseudocode to detect the gum line for the segmentation of steps 26 and 28.

TABLE 1

Connected Components Algorithm for Gum Line Finding

Input: a 3D mesh representing a tooth with gums.
Output: A subset of the input 3D mesh representing only the tooth.
Method steps:
1  Calculate the adjacency matrix of the mesh.
2  Calculate the concavity at each vertex of the mesh.
3  Create a filtered adjacency matrix by removing edges from the original adjacency matrix where the absolute difference in concavity is greater than a certain threshold.
4  Find the connected components of the filtered adjacency matrix, and ignore components that have smaller than a certain number of vertices.
5  Clean the remaining components by dilating them repeatedly then eroding them repeatedly along the original mesh. The components should each contain either tooth or gum, but not both. The tooth and especially gum may be over-segmented.
6  Apply a method to identify which regions or regions represent the tooth. For example, find the appropriate extreme z-value of the original mesh and choose the regions which are within a certain number of millimeters.
7  Merge the regions representing the tooth into a single mesh.

Figure 4:
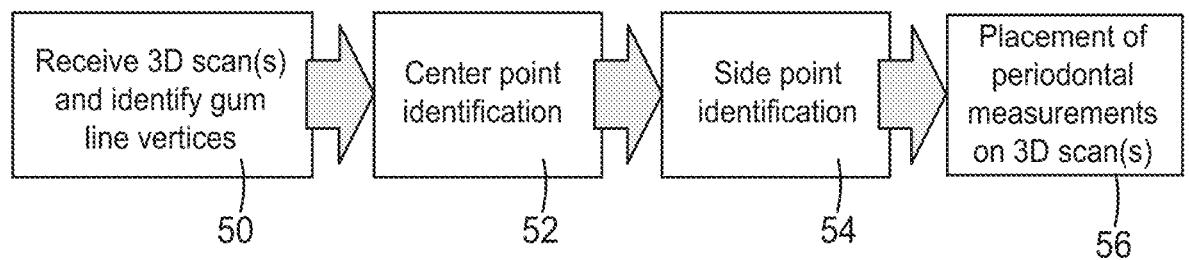
FIG. 4 is a flow diagram of a method for displaying periodontal measurements on 3D scans.

FIG. 4 is a flow diagram of a method for displaying periodontal measurements on 3D scans such as scans 1 and 2 referenced in the flow diagram of FIG. 3. As shown in FIG. 4, this method receives one or more 3D scans and finds the gum line vertices by extracting the borders of the segmentation of teeth from gingiva (step 50). One of several methods can subsequently be used to identify the center point (step 52). A first option is to identify the middle vertex in the list of gum line vertices. A second option is to re-align the vertices along the principal axes derived using principle component analysis, then find the peak of the curve by finding the point at which the slope changes sign (i.e., zero-valued derivative). A third option is to use anatomical information about the segmented tooth itself to find the midpoint. Such information could include the up-down axis of the tooth or, for cuspids, bicuspids, and molars, the location of the cusp tips.

The method identifies side points (step 54), and side point identification can also proceed one of several ways. One option is to identify the points closest to boundaries between each tooth and its neighboring teeth. Another option is to identify points that lie a given distance, d, from the center along the gum line points. Alternatively, the side points can be identified as the points a given height, h, from the principal component analysis (PCA)-oriented vertices. As with the center points, anatomical information about the segmented tooth can also be used to find the side points.

Figure 5:
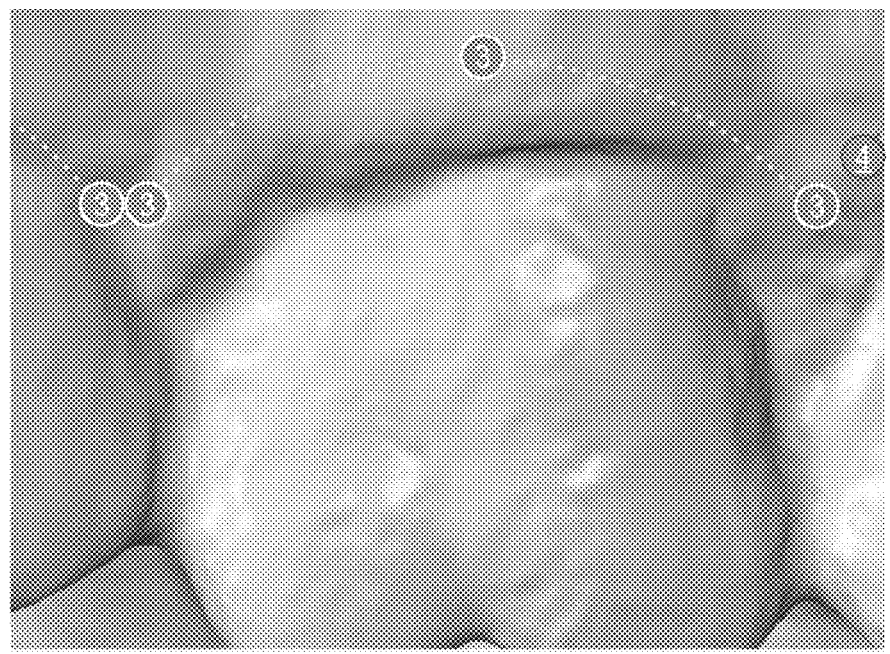
FIG. 5 is an image illustrating periodontal measurements on a 3D scan.

The method also includes placement of periodontal measurements on or proximate to the one or more 3D scans (step 56). Identification of the periodontal measurements can either be placed at the center-side point locations directly or at an offset from these locations. Periodontal measurements from previous visits can also be displayed to demonstrate changes in dental status between visits. FIG. 5 is an image illustrating periodontal measurements placed upon a 3D scan or digital 3D model. The placement of periodontal measurements can include, but is not limited to, the following: overlaying or superimposing the measurements on the scans; showing the measurements in a side-by-side view with the scans; and using hover text to show the measurements on the scans.

The registration for steps 30 and 38 involves obtaining segmented digital 3D models of a tooth and gingiva from scanning the tooth at two different times, and rotating and translating the models to align them together for use in detecting changes in the two models. In particular, registration is the process of aligning or obtaining the best fit rotation and translation that needs to be applied to a moving mesh to align with the fixed mesh or generalized to multiple meshes.

In an exemplary embodiment, the registration can use the iterative closest point (ICP) algorithm to achieve registration between meshes representing the digital 3D models. One variant of the ICP algorithm includes the steps in Table 2. For the exemplary embodiment, the registration (with reference to the steps in Table 2) uses all points in step 1, Euclidean and point to plane in step 2, equal weights of pairs and rejecting them based on a fixed predetermined threshold (steps 3 and 4), sum of squared distances as the metric in step 5, and minimization is achieved in step 6 using singular value decomposition (SVD) and levenberg marquart methods.

Optionally, once a final registration optimum has been reached, one could verify that this is indeed a stable optimum. This can be done in two possible ways—first, by perturbing the optimum by small amounts of rotation and translation to determine if it converges back to the original optimum or whether a better optimum can be reached; second, by performing random restarts of the ICP algorithm with varying amounts of initial rotation and translation to determine the best optimum among those reached for each initialization.

TABLE 2

ICP Algorithm Steps

1 Selection of points in the meshes to be registered. There are a few ways to select these points:
  a. Select all points
  b. Select a random subsample
  c. Uniformly subsample
  d. Select points corresponding to key features such as curvature and local covariance
2 Finding matching (corresponding) points is the step in which the closest point in the second mesh for every point in the first mesh is determined using a suitable distance metric. This step can also be achieved using different metrics:
  a. Euclidean point to point distance
  b. Point to plane distance or distance along normal
  c. Reverse calibration
  d. Other combinations
3 Weighting of pairs corresponds to ranking the correspondences. This can be done using some weights based on distances, weights based on normal direction compatibility, or other factors.
4 Rejecting pairs can be done using thresholds on the weights computed in the previous step among other heuristics.
5 Error metric for optimization can be calculated as the sum of the squared distances between the pairs remaining after step 4. The distances can also be point to plane distance as in step 2.
6 Optimization can be done using SVD (singular value decomposition), levenberg marquart optimization, BFGS, stochastic gradient descent, simulated annealing, or other techniques.

Figure 6:
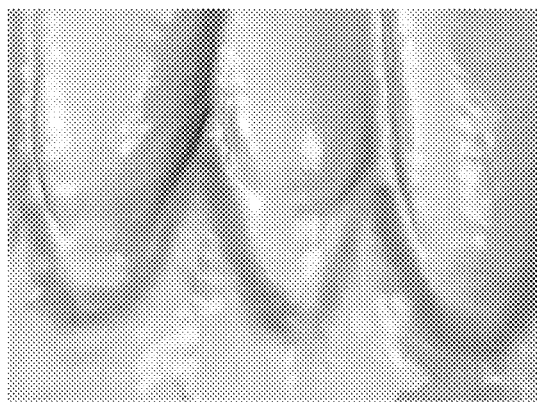
FIGS. 6 and 7 are images illustrating gum line changes or recession as an effect that changes location between the images.
Figure 7:
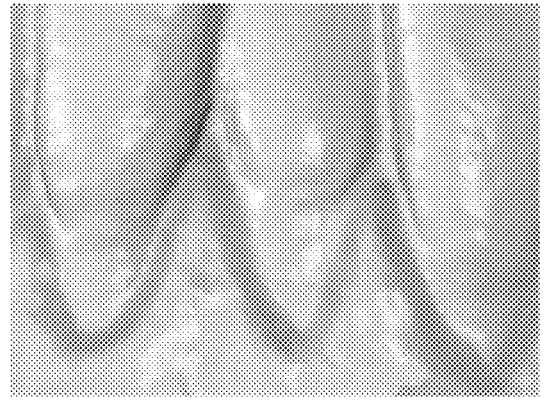
Figure 8:
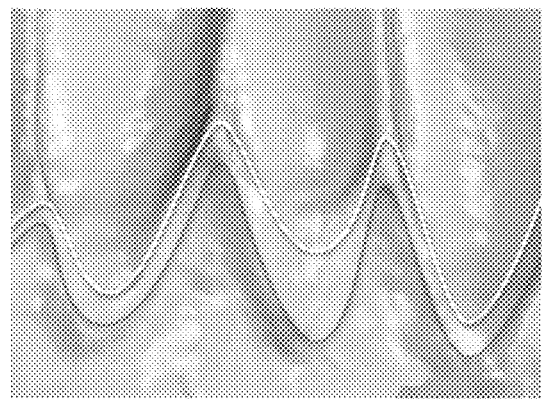
FIG. 8 is an image illustrating gum line changes or recession displayed as two lines superimposed on a 3D scan.

The registration in steps 30 and 38 provides an indication in changes of the gum line between the registered 3D scans for comparing the gum lines in steps 32 and 40. The gum line comparison can be used to generate a gum line change map for step 34, and an estimated gum line change map for step 44, to illustrate the gum line change, which can be displayed as an effect (e.g., shadow or line) that changes location between meshes, illustrated in FIGS. 6 and 7, or as two lines superimposed on a single mesh as illustrated in FIG. 8. A transformation matrix is first applied to associate a tooth border from the previous scan to the current scan. Effects such as color or shadow can subsequently be inserted at the location of the tooth border on the current scan. Optionally, gum line smoothing can also be performed before or after applying the transformation.

From the output shown in FIG. 8, quantitative gum line change, such as gum line recession, measurements can also be achieved by measuring the distance between corresponding points in the two segmentations. Corresponding points can be identified using one of several options including minimum distance (Euclidean distance or path length along the mesh) between points, distance between points in a fixed direction, or distance between points along the direction defined by the normal to the tangent line on one of the segmentations.

Corresponding gum line point identification can also facilitate rendering of the incremental changes that occurred between the first and second scans. These incremental changes can be shown as a series of images or a video representing gum line changes over time. First, linear or non-linear interpolation between corresponding points is performed. The closest point on the mesh for each interpolated point is then identified. A new incremental time point gum line rendering is subsequently formed by joining the interpolated points and optionally performing smoothing. Linear or non-linear extrapolation can also be applied to enable rendering of changes that may occur in the future.

Quantitative recession measurements may be used to facilitate an accentuated effect (e.g., more pronounced shadow) in regions displaying more extreme changes. For example, the size and darkness of the shadow effect can be scaled dependent on the magnitude of the measured gum line recession measurements. This visualization technique is not limited to gum line recession display. Rather, accentuated shadow or contrast effect can be used generally to visually communicate quantitatively measured changes between scans.

Figure 9:
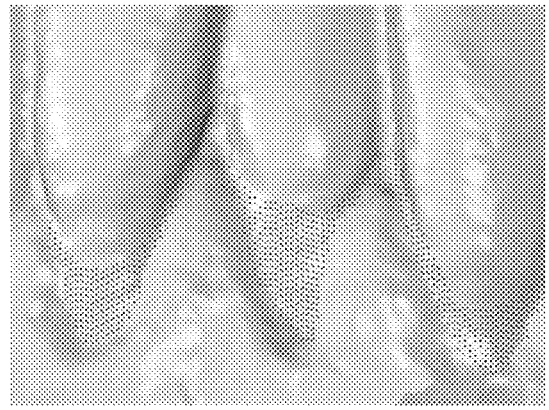
FIG. 9 is an image illustrating gum line changes or recession displayed as an area between two gum line segmentations.

Gum line change or recession can also be presented as an area between two gum line segmentations as illustrated in FIG. 9. A transformation is applied to the full mesh in the previous scan to associate it with the current scan. The closest point in the current scan to each point in the previous scan is assigned the label given in the previous scan. Points demonstrating recession, shown for example in a particular color, are identified as those assigned a gum label in the previous scan and a tooth label in the current scan.

Periodontal measurements, also illustrated in FIG. 5, can also be placed on the gum line change maps such as those maps shown in FIGS. 6-9.

The invention claimed is:

1. A method for displaying periodontal measurements, comprising steps of executed by a processor:
   receiving first and second digital 3D models of teeth and gingiva, wherein the first digital 3D model was taken at a first time, and the second digital 3D model was taken at a second time later than the first time;
   segmenting the first and second digital 3D models to digitally identify the teeth from the gingiva and generate gingiva segmented first and second digital 3D models;
   receiving first periodontal measurements relating to the first digital 3D model and second periodontal measurements relating to the second digital 3D model;

identifying side points of the first or second digital 3D model by using anatomical information about the segmented teeth to find the side points; and displaying the first and second periodontal measurements placed upon the first or second digital 3D model directly at or at an offset from one or more of the side points, wherein the display of the first and second periodontal measurements demonstrates changes between the first and second digital 3D models.

2. The method of claim 1, further comprising, executed by the processor, comparing the gingiva segmented first and second digital 3D models to detect gum line changes by determining differences between the gingiva segmented first digital 3D model and the gingiva segmented second digital 3D model where the differences relate to the gum line, and wherein the displaying step comprises displaying an indication of the gum line changes.

3. The method of claim 2, wherein the displaying step comprises displaying a gum line change map.

4. The method of claim 3, wherein the displaying step comprises displaying a first line illustrating a position of the gum line in the first digital 3D model and displaying a second line illustrating a position of the gum line in the second digital 3D model.

5. The method of claim 3, wherein the displaying step comprises displaying shading illustrating a difference in positions of the gum lines in the first and second digital 3D models.

6. The method of claim 3, wherein the displaying step comprises displaying an area illustrating a difference in positions of the gum lines in the first and second digital 3D models.

7. The method of claim 1, wherein the anatomical information includes up-down axes of the teeth.

8. A method for displaying periodontal measurements, comprising steps of executed by a processor:

receiving first and second digital 3D models of teeth and gingiva, wherein the first digital 3D model was taken at a first time, and the second digital 3D model was taken at a second time later than the first time;

segmenting the first and second digital 3D models to digitally identify the teeth from the gingiva and generate gingiva segmented first and second digital 3D models;

receiving first periodontal measurements relating to the first digital 3D model and second periodontal measurements relating to the second digital 3D model;

identifying center points of the first or second digital 3D model by using anatomical information about the segmented teeth to find the center points; and displaying the first and second periodontal measurements placed upon the first or second digital 3D model directly at or at an offset from one or more of the center points, wherein the display of the first and second periodontal measurements demonstrates changes between the first and second digital 3D models.

9. The method of claim 8, further comprising, executed by the processor, comparing the gingiva segmented first and second digital 3D models to detect gum line changes by determining differences between the gingiva segmented first digital 3D model and the gingiva segmented second digital 3D model where the differences relate to the gum line, and wherein the displaying step comprises displaying an indication of the gum line changes.

10. The method of claim 9, wherein the displaying step comprises displaying a gum line change map.

11. The method of claim 10, wherein the displaying step comprises displaying a first line illustrating a position of the gum line in the first digital 3D model and displaying a second line illustrating a position of the gum line in the second digital 3D model.

12. The method of claim 10, wherein the displaying step comprises displaying shading illustrating a difference in positions of the gum lines in the first and second digital 3D models.

13. The method of claim 10, wherein the displaying step comprises displaying an area illustrating a difference in positions of the gum lines in the first and second digital 3D models.

14. The method of claim 8, wherein the anatomical information includes up-down axes of the teeth.

15. A computer-implemented method for displaying a user interface comprising periodontal measurements, wherein:

the user interface displays a first or second digital 3D model of teeth and gingiva, displays first periodontal measurements relating to the first digital 3D model, and displays second periodontal measurements relating to the second digital 3D model;

the first digital 3D model was taken at a first time, and the second digital 3D model was taken at a second time later than the first time;

the first and second digital 3D models are segmented to digitally identify the teeth from the gingiva and generate gingiva segmented first and second digital 3D models;

the display of the first and second periodontal measurements demonstrates changes between the first and second digital 3D models;

the user interface displays the first and second periodontal measurements directly at or at an offset from one or more of side points and center points of the first or second digital 3D model; and the side points and the center points are identified by using anatomical information about the segmented teeth to find the side points and the center points.

16. The method of claim 15, wherein the user interface displays an indication of gum line changes between the first and second digital 3D models.

17. The method of claim 15, wherein the anatomical information includes up-down axes of the teeth.

* * * * *